US009968756B2

United States Patent
Tsai et al.

(10) Patent No.: US 9,968,756 B2
(45) Date of Patent: May 15, 2018

(54) PRESSURE RELIEF APPARATUS WITH BRAIN ENTRAINMENT

(71) Applicant: Industrial Technology Research Institute, Hsinchu (TW)

(72) Inventors: Shu-Hui Tsai, Hsinchu County (TW); Szu-Shan Shieh, Taipei (TW); Chin-Jung Kuo, Hsinchu (TW); Hsien-Cheng Liao, Taipei (TW); Hung-Jung Lin, Miaoli County (TW)

(73) Assignee: Industrial Technology Research Institute, Hsinchu (TW)

( * ) Notice: Subject to any disclaimer, the term of this patent is extended or adjusted under 35 U.S.C. 154(b) by 994 days.

(21) Appl. No.: 13/917,644

(22) Filed: Jun. 14, 2013

(65) Prior Publication Data

US 2014/0371516 A1 Dec. 18, 2014

(51) Int. Cl.
*A61M 21/02* (2006.01)
*A61B 5/00* (2006.01)
(Continued)

(52) U.S. Cl.
CPC .......... *A61M 21/02* (2013.01); *A61B 5/0205* (2013.01); *A61B 5/4035* (2013.01);
(Continued)

(58) Field of Classification Search
CPC ................. A61M 21/00; A61M 21/02; A61M 2021/0022; A61M 2021/0044;
(Continued)

(56) References Cited

U.S. PATENT DOCUMENTS 5,267,942 A    12/1993   Saperston
5,356,368 A    10/1994   Monroe
(Continued)

FOREIGN PATENT DOCUMENTS

CA       2205654 A1    5/1996
CA       2364032 A1    9/2000
(Continued)

OTHER PUBLICATIONS

"Notice of Allowance of Taiwan Counterpart Application", dated Mar. 18, 2014, p. 1-p. 5.
(Continued)

*Primary Examiner* — Catherine B Kuhlman
*Assistant Examiner* — Carrie R Dorna
(74) *Attorney, Agent, or Firm* — JCIPRNET (57) ABSTRACT

A pressure relief apparatus with brain entrainment includes a resonant wave generating module and a bio-signal measuring unit. The resonant wave generating module includes multiple resonant devices, divided into multiple regions. Each of the resonant regions can respectively generate a resonant wave being changeable or turned off. The bio-signal measuring unit at least measures an energy of autonomic sympathetic nerve system LH and an energy of autonomic parasympathetic nerve system HF. According to a current one of a set of present conditions, a set of feedback control signals is output to the resonant wave generating module to modulate the resonant devices.

18 Claims, 9 Drawing Sheets

(51) Int. Cl.
*A61B 5/0205* (2006.01)
*A61N 2/12* (2006.01)
*A61N 2/00* (2006.01)
*A61M 21/00* (2006.01)
*A61B 5/024* (2006.01)

(52) U.S. Cl.
CPC ............ *A61B 5/4836* (2013.01); *A61B 5/742* (2013.01); *A61B 5/02405* (2013.01); *A61M 2021/005* (2013.01); *A61M 2021/0022* (2013.01); *A61M 2205/3303* (2013.01); *A61M 2205/502* (2013.01); *A61M 2230/06* (2013.01); *A61M 2230/08* (2013.01); *A61N 2/004* (2013.01); *A61N 2/12* (2013.01)

(58) Field of Classification Search
CPC .... A61M 2021/005; A61M 2021/0027; A61M 2021/0061; A61M 2021/0088; A61N 1/40; A61N 1/403
See application file for complete search history.

(56) References Cited

U.S. PATENT DOCUMENTS

| | | | |
|---|---|---|---|
| 5,365,939 A | 11/1994 | Ochs | |
| 5,403,261 A | 4/1995 | Shimizu et al. | |
| 6,071,229 A | 6/2000 | Rubins | |
| 6,123,661 A | 9/2000 | Fukushima et al. | |
| 6,358,201 B1 | 3/2002 | Childre et al. | |
| 6,845,520 B2 | 1/2005 | Kim | |
| 7,163,512 B1 | 1/2007 | Childre et al. | |
| 7,462,151 B2 | 12/2008 | Childre et al. | |
| 7,674,224 B2 | 3/2010 | Hewett | |
| 7,715,910 B2 | 5/2010 | Hargrove et al. | |
| 2002/0198438 A1* | 12/2002 | Cromer | A61M 21/02 600/27 |
| 2003/0195383 A1 | 10/2003 | Yoon | |
| 2004/0002635 A1 | 1/2004 | Hargrove et al. | |
| 2005/0153268 A1 | 7/2005 | Junkin et al. | |
| 2006/0030907 A1* | 2/2006 | McNew | A61B 5/02405 607/88 |
| 2006/0258950 A1 | 11/2006 | Hargrove et al. | |
| 2007/0021675 A1 | 1/2007 | Childre et al. | |
| 2007/0084473 A1 | 4/2007 | Hewett | |
| 2007/0270668 A1 | 11/2007 | Childre et al. | |
| 2008/0039750 A1 | 2/2008 | Mahmoud | |
| 2008/0269652 A1 | 10/2008 | Reiner | |
| 2009/0137915 A1 | 5/2009 | Childre et al. | |
| 2009/0264952 A1 | 10/2009 | Jassemidis et al. | |
| 2010/0204750 A1 | 8/2010 | Hargrove et al. | |
| 2011/0015470 A1 | 1/2011 | Lenhardt et al. | |
| 2012/0143107 A1* | 6/2012 | Henley | A61H 1/001 601/53 |

FOREIGN PATENT DOCUMENTS

| | | |
|---|---|---|
| CA | 2364032 C | 8/2008 |
| CN | 2408893 | 12/2000 |
| CN | 1358074 A | 7/2002 |
| CN | 1739817 | 3/2006 |
| CN | 101428163 | 5/2009 |
| CN | 101623532 | 1/2010 |
| CN | 201379899 | 1/2010 |
| DE | 19723138 | 12/1998 |
| EP | 2276536 A1 | 1/2011 |
| JP | 9220284 | 8/1997 |
| JP | 2002258880 | 9/2002 |
| JP | 2005312755 | 11/2005 |
| JP | 2009201606 | 9/2009 |
| JP | D1473192 | 6/2013 |
| TW | D152308 | 3/2013 |
| WO | 9615716 A1 | 5/1996 |
| WO | 0051677 A2 | 9/2000 |
| WO | 0051677 A3 | 4/2001 |
| WO | 03066157 A2 | 8/2003 |
| WO | 2006019822 A2 | 2/2006 |
| WO | 2006019822 A3 | 4/2006 |
| WO | 2009089140 A2 | 7/2009 |
| WO | 2009089140 A3 | 9/2009 |
| WO | 2009126330 A1 | 10/2009 |

OTHER PUBLICATIONS

"Office Action of Taiwan Counterpart Application", dated Nov. 13, 2013, p. 1-p. 4.
"Office Action of China Counterpart Application", dated Jun. 5, 2014, p. 1-p. 5.

* cited by examiner

PRESSURE RELIEF APPARATUS WITH BRAIN ENTRAINMENT

BACKGROUND

Technical Field

The disclosure is directed to a pressure relief apparatus with brain entrainment, in which Schumann waves are further adopted to generate brain entrainment.

Related Art

Pressure relief and relaxation are human instincts. Conventional pressure relieving methods are based on five senses, and many related researches and products have been launched. However, factors that actuate the five senses and the autonomic nervous operation remain a complex system, and whether there is an operation mode for physical and mental in common still attracts curiosity and discussion from everyone.

Since the time when researches in regard to brainwave science and autonomic nerve system, there are some products attempting guidance of higher-level consciousness, and as a result, many new product applications are produced. The conventional method for the five experiencing pressure relief also associates with brainwave resonances. However, related aids for pressure relief fails to effectively provide parameters corresponding to physical and metal pressure relief qualitatively and quantitatively for perception feedback (e.g. a corresponding relationship between descriptive characteristics of proprioception and human factors) of the pressure relief aids and the five sense experiences. Moreover, fails to achieve the ultimate effects and targets for pressure relief due to incapability of dynamical and immediate feedback adjustment according to the physiological states.

Accordingly, how to provide a pressure relief technique with effective and immediate feedback of physiological states is an important subject of research and development topics at present.

SUMMARY

The disclosure introduces a pressure relief apparatus with brain entrainment capable of applying vibrations corresponding to Schumann waves on different parts of a human body to generate resonance so as to achieve an effect of brain entrainment for pressure relief.

The disclosure introduces a pressure relief apparatus with brain entrainment, including a resonant wave generating module and a bio-signal measuring unit. The resonant wave generating module includes a plurality of resonant devices divided into a plurality of resonant regions. Each of the resonant regions can respectively generate a resonant wave being changeable or turned off. The bio-signal measuring unit at least measures an energy of autonomic sympathetic nerve system, also represented by LH, and an energy of autonomic parasympathetic nerve system, also represented by HF, of a user. According to one of a set of preset conditions, a set of feedback control signals is output to the resonant wave generating module to modulate the resonant devices.

Several exemplary embodiments accompanied with figures are described in details below to further describe the disclosure in details.

BRIEF DESCRIPTION OF THE DRAWINGS

The accompanying drawings are included to provide further understanding, and are incorporated in and constitute a part of this specification. The drawings illustrate exemplary embodiments and, together with the description, serve to explain the principles of the disclosure.

DETAILED DESCRIPTION OF DISCLOSED EMBODIMENTS

The disclosure introduces a pressure relief apparatus based on the utilization of physiological signals of an individual as feedback, such that an objective evaluation method is adopted with the exclusion of subjective feelings of a user. Accordingly, an actually measured physiological state is used as the feedback to achieve an effect of pressure relief. Moreover, in the disclosure, a setting mode for individual experiences and a specific guiding mode are also provided to meet demands for physical and mental feelings.

In the related art, most products for pressure relief works according to processes that have been already set. However, in the disclosure, feedback of physiological signals is utilized to operate and control pressure relief manners, and therein, a method of pressure relief with brain entrainment is further utilized. Physical constitutions and physiological states of people are different by time and thus, by implementing the pressure relief based on a current physiological state of an individual, a better effect of pressure relief will be obtained.

The disclosure is directed to a pressure relief apparatus with biofeedback for brain entrainment and more particularly, a pressure relief apparatus having interfaces for operating and generating the brain entrainment by utilizing parameter signals of heart rate variability (HRV) output from the autonomic nerve system and combining a resonant wave of a Schumann wave to achieve an experience of complete relaxation. In the pressure relief apparatus with biofeedback for brain entrainment introduced by the disclosure, parameter signals of currently measured heart rate variability are utilized to control multi-channel resonant wave generators of Schumann waves so as to achieve various types of brain entrainment states. A relative degree of tense and relaxation with respect to each physical pressure relief state is represented by using a parameter signal of heart rate variability (e.g., an energy degree of autonomic nerve system), which includes a total energy, a sympathetic energy, a parasympathetic energy and so on of the autonomic nerve system and configured as feedback of physical and mental state. In an exemplary embodiment, a degree of the feedback is evaluated based on testing sympathetic and parasympathetic factors. Further, the parameters may be used to control scenario pictures for the pressure relief and provide scenario-based perceptional interaction. Array type multi-channel Schumann wave generators having various frequency bands and spatial distributions are used to guide the brain entrainment to be generated according to different modes, such as constitution, day, night and auxiliary constitution of each person and micro vibrations of multi-channel Schumann waves matching the human body so as to provide more adaptive feedback entrainment. The pressure relief apparatus with biofeedback for brain entrainment may be embedded into a bed, a chair or a floor to provide a realistic sense of interaction.

Exemplary embodiments are provided below to describe the disclosure, though the disclosure is not limited to the provided exemplary embodiments, and the provided exemplary embodiments can be suitably combined.

The disclosure introduces a pressure relief apparatus with brain entrainment, in which for example, a multi-channel Schumann wave brain entrainment module for feedback of physiological signals is utilized with output signals of the physiological signal, such as sympathetic and parasympathetic parameters of autonomic nerve system, so as to meet immediate feedback adjustments of the human body in response to stimulations of different dynamic ranges during pressure relief. Thereby, feedback physiological signals are output to control output modes of the multi-channel Schumann wave brain entrainment module and scenario changes for pressure relief is set.

The physiological signal output includes signals related to the autonomic nerve system containing non-linear and statistical parameters, such as a energy of autonomic sympathetic nerve system LH, and an energy of autonomic parasympathetic nerve system HF, a heartbeat interval (R-R interval, RRI), a heart rate variability coefficient (SDNN), a total power (TP) of autonomic nerve system. Among them, the heartbeat of a human body is not in a constant speed, and generally called a heart rate variability (HRV). Even though in a calm and stable state, the human body has a considerable degree of change due to different physical relaxing conditions. The HRV is controlled by the automatic nervous system (ANS) so as to keep physical and mental balance.

Furthermore, the disclosure introduces an array multi-channel Schumann wave entrainment feedback for strengthening brain entrainment of an experiencing person to produce perceptional interaction so as to provide more adaptive feedback entrainment. The pressure relief module with the biofeedback for brain entrainment may be embedded into a bed, a chair or a floor to provide a perceptional interaction.

The multi-channel Schumann wave brain entrainment module may be combined with the output signals of the physiological signal and Schumann wave entrainment feedback, and the signals may be combined with data, such as animations, scenario designs, network applications (APP) and cloud data to provide more perceptional and open-expandable scenarios for experiencing pressure relief.

The disclosure introduces a pressure relief apparatus with brain entrainment, which includes, for example, a resonant wave generating module and a bio-signal measuring unit. The resonant wave generating module includes a plurality of resonant devices divided into a plurality of resonant regions. Each of the resonant regions respectively generates a resonant wave being changeable or turned off. The bio-signal measuring unit at least measures energy of autonomic sympathetic nerve system LH and an energy of autonomic parasympathetic nerve system HF of a user and, according to one of the set of preset conditions, outputs a set of feedback control signals to the resonant wave generating module to modulate the resonant devices.

Moreover, the pressure relief apparatus with brain entrainment may also include a display and be connected with an application and a database of a network.

Schumann waves occurs in a cavity resonator formed by the earth surface and an ionosphere which is approximately 100 miles from the earth surface and varies with the strength of the sunlight, wherein the cavity resonator functions like drumming. The Schumann waves have a extremely low frequency and is capable of penetrating through any substance, including human beings on the earth surface. A human brain has $\alpha$ band, $\beta1$ band and $\beta2$ band that are corresponding to the Schumann waves. Some researches have pointed out that the Schumann waves makes an impact on organisms, and if a human body is often immersed by the Schumann waves, he/she would be possible to receive harmonic resonances which facilitates in physical and mental development.

According to researches related to resonance phenomenon, if a vibration wave source having a constant frequency is applied from the external to a plurality of resonance bodies chaotic phases/frequencies at an initial stage, after a period of time, the resonance bodies results in having the same phase and frequency as the externally applied vibration wave source. The disclosure utilizes the externally applied Schumann waves to modulate the harmonic resonances for physical and mental pressure relief.

Figure 1:
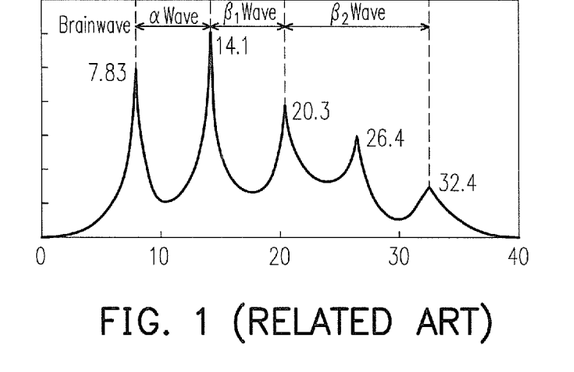
FIG. 1 is a schematic diagram showing a relationship between overtones in a Schumann wave and a brainwave.

The disclosure proposes the utilization of entrainment frequencies of multi-channel Schumann waves for hybrid micro-vibration resonance to achieve "brain entrainment" for pressure relief. With feedback of physiological signals, the physiological signals output from the autonomic nerve system are combined to modulate different modes for pressure relief so as to meet various types of demands for human beings during pressure relief. By doing so, the physiological signals are output to modulate frequency amplitudes and frequency distribution systems required for pressure relief. FIG. 1 is a schematic diagram showing a relationship between overtones in a Schumann wave and a brainwave. Referring to FIG. 1, α band, β1 band and β2 band in a brainwave of a human brain has a corresponding relationship with peaks of the overtones in the Schumann wave, and herein, the peaks are represented by 7.83 Hz, 14.1 Hz and 20.3 Hz. In the disclosure, an entrainment wave source, which is, for example, equivalent to the Schumann wave, is provided according to spectral characteristics of the Schumann wave so as to generate entrainment for pressure relief. Meanwhile, with measured physiological signals, a pressure relief mode conformed to a natural physiological rhythm for a human day and night is determined in response to currently measured relevant signals.

Figure 2:
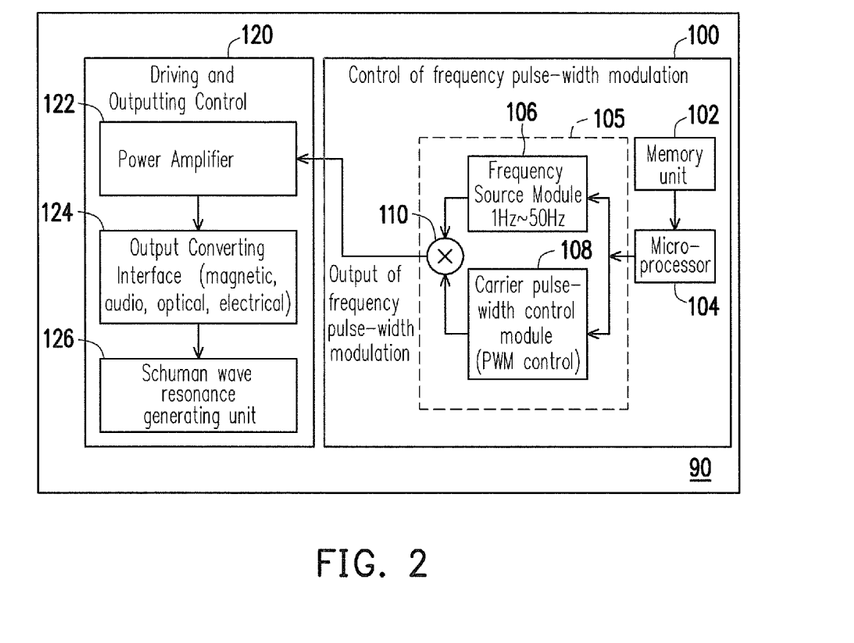
FIG. 2 is a schematic block diagram showing a resonant wave generating module according to an exemplary embodiment of the disclosure.

FIG. 2 is a schematic block diagram showing a resonant wave generating module according to an exemplary embodiment of the disclosure. Referring to FIG. 2, a resonant wave generating module 90 includes a frequency and pulse-width modulation unit 100 and a resonant device 120. The frequency and pulse-width modulation unit 100 includes, for example, a memory unit 102, a micro-processor 104 and a modulation module 105. The modulation module 105 includes a frequency source module 106, carrier pulse-width control module 108 and a multiplier 110. The frequency and pulse-width modulation unit 100 may generate an output for frequency and pulse-width modulation and input the same to the resonant device 120 to generate a resonant wave, such as an artificial Schumann wave. That is, the resonant wave is artificially generated corresponding to a frequency peak band of the Schumann wave and may simulate at least a portion of the band of an actual Schumann wave upon combination. The modulation module 105 is controlled by the micro-processor 104 to generate the output for frequency and pulse-width modulation. The memory unit 102 is configured to provide a waveform, such as a waveform of a square wave to the micro-processor 104 for modulation. There are many types of circuit designs for the frequency and pulse-width modulation unit 100 may have various types of circuitry designs, and is not limited to a specific circuit.

The resonant device 120 includes, for example, a power amplifier 122, an output converting interface 124 and a Schumann wave resonance generating unit 126. The resonant device 120 converts a wave into a resonant wave according to a frequency and α bandwidth as required. The power amplifier 122 amplifies an input signal so as to drive the output converting interface 124 to convert the signal into, for example, a magnetic signal, an audio signal, an optical signal or an electrical signal, to control the Schumann wave resonance generating unit 126 to artificially generate a Schumann wave source. The resonant device 120 is, for example, an integrated vibration motor and will be described below. The resonant device 120 is configured to generate a resonant wave source according to the input frequency, and namely, a device that can achieve the same effect as the resonant device 120 is sufficient.

Overall speaking, based on a multi-channel design, a plurality of resonant devices 120 is adopted and divided into a plurality of regions. Each of the regions is controlled by a modulation module 105 so as to achieve respective control of multiple channels.

Figure 3:
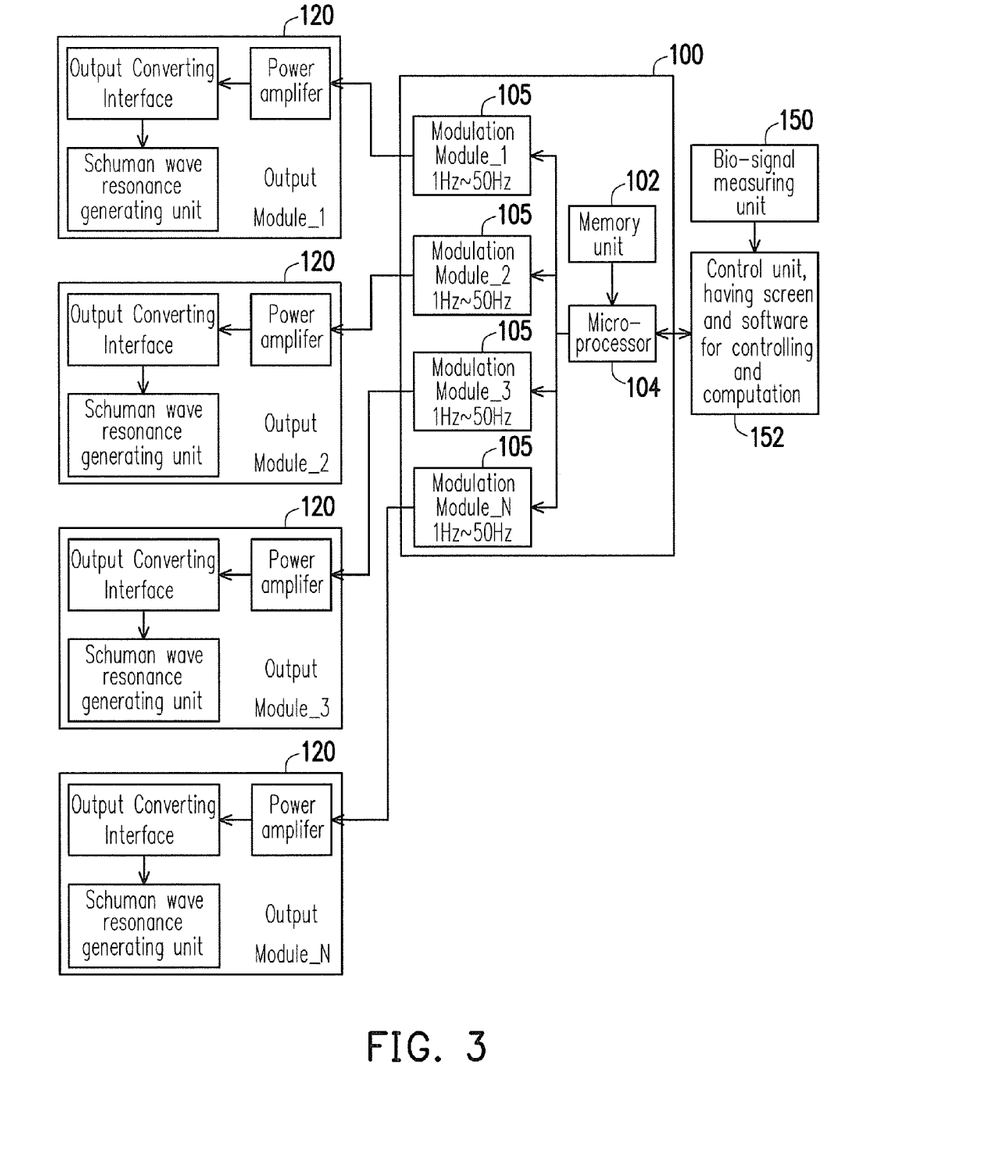
FIG. 3 is a schematic block diagram showing a circuitry of a pressure relief apparatus with brain entrainment according to an exemplary embodiment of the disclosure.

FIG. 3 is a schematic block diagram showing a circuitry of a pressure relief apparatus with brain entrainment according to an exemplary embodiment of the disclosure. Referring to FIG. 3, the basic elements illustrated in FIG. 2 may design in a multi-channel configuration to form the pressure relief apparatus with brain entrainment. The pressure relief apparatus with brain entrainment may include a resonant wave generating module 90 and a bio-signal measuring unit 150. The resonant wave generating module 90 includes the frequency and pulse-width modulation unit 100 and a plurality of resonant devices 120 divided into a plurality of resonant regions, such as into N resonant regions having output modules 1 through N. Each of the resonant regions may respectively generate a resonant wave being changeable or turned off. Each of the resonant devices 120 is controlled on a changeable frequency by a plurality of modulation modules 105 of the frequency and pulse-width modulation unit 100. The frequency belongs to a frequency range of a Schumann wave.

The bio-signal measuring unit 150 measures a biofeedback parameter, which measures, for example, at least an energy of autonomic sympathetic nerve system LH and an energy of autonomic parasympathetic nerve system HF of a user. The energy of autonomic sympathetic nerve system generally belongs to a low frequency and represented by LH, while the energy of autonomic parasympathetic nerve system generally belongs to a high frequency and represented by HF. A control unit 152 is also included and can be a personal computer with a screen and software for controlling and computation, as an example.

The control unit 152 receives the biofeedback parameter measured from the user and according to one of a set of preset conditions, outputs a set of feedback control signals to the frequency and pulse-width modulation unit 100 of the resonant wave generating module 90 so as to control each of the resonant devices 120, respectively. From a broader point of view, the control unit 152 may also be integrated in one functional block of the frequency and pulse-width modulation unit 100. Accordingly, the pressure relief apparatus with brain entrainment may include the resonant wave generating module 90 and the bio-signal measuring unit 150.

It should be noted that for providing the same function, the actual circuitry design may have a variety of modifications without limitations. An exemplary embodiment is provided below for descriptions.

Figure 4:
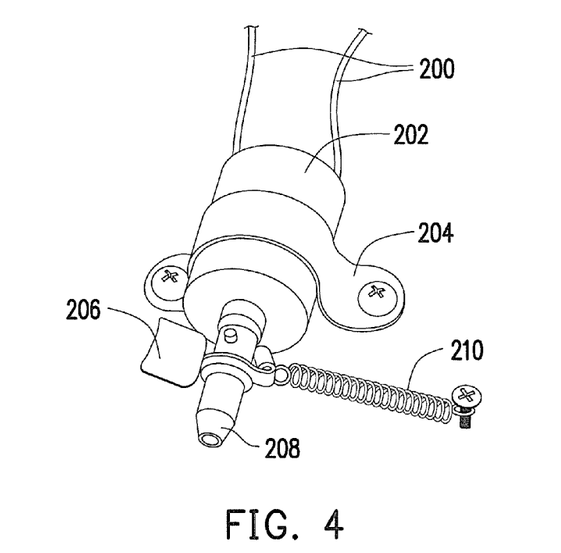
FIG. 4 is a schematic diagram showing a structure of the resonant device according to an exemplary embodiment of the disclosure.

FIG. 4 is a schematic diagram showing a structure of a resonant device according to an exemplary embodiment of the disclosure. Referring to FIG. 4, the resonant device 120, as an example, includes a plurality of vibration motors. Each vibration motor includes a motor 202, which is input with a signal (e.g. a pulse voltage signal that will be described with reference to FIG. 5) of a predetermined frequency via a power cord 200. The motor 202 rotates according to the pulse voltage signal having a predetermined pulse width upon being amplified, and a shaft 208 of the rotation rotates for an angle according to the pulse width. The motor 202 is disposed on a required substrate by a fastening element 204. The substrate may be a rigid flexible material for conforming to a main apparatus where the substrate is embedded. A damping element 210, such as a spring, returns the shaft 208 to its original position when the voltage is zero so as to achieve the shaft 208 the rotating back and forth according to the frequency. When a vibrator 206 is fastened to the shaft 208, a resonant wave is generated as the air is perturbed due to the shaft 208 rotating back and forth. The frequencies of the resonant wave are controlled at or near frequency peaks of the Schumann wave corresponding to the bands of the brain wave. Thereby, the frequencies given by the brain wave is entrained.

Generally speaking, there are other ways to generate the resonant wave. Though in the present exemplary embodiment, only the implementation by using the motors is illustrated, the disclosure is not limited to the implementation way.

Figure 5:
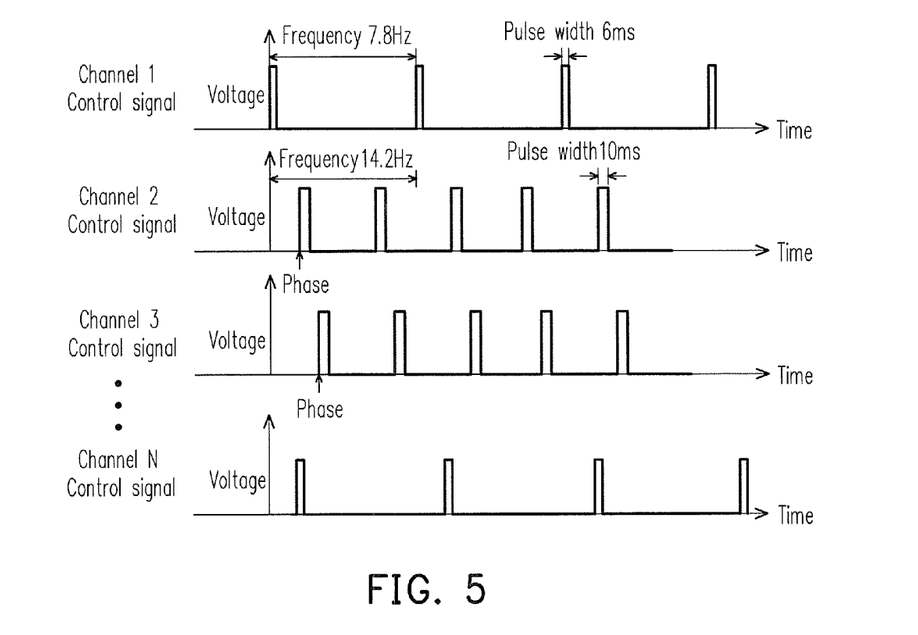
FIG. 5 is a schematic diagram showing signals of channels according to an exemplary embodiment of the disclosure.

FIG. 5 is a schematic diagram showing signals of channels according to an exemplary embodiment of the disclosure. Referring to FIG. 5, voltage signals of the motor are modulated corresponding to different channels and thereby, operation frequencies of the motor are respectively controlled. Since different channels correspond to different body parts of the user, a better effect of pressure relief may be achieved by the respective control. The relationship between the channels and the body parts will be described later.

In the present exemplary embodiment, channel 1 has a frequency of, for example, 7.8 Hz adjacent to a peak of a Schumann wave and a pulse width of, for example, 6 ms by which a rotation magnitude of the motor is determined. Channel 2A has a frequency of, for example, 14.2 Hz adjacent to another peak of the Schumann wave and a pulse width of, for example, 10 ms by which another rotation magnitude of the motor is determined by the pulse width and a phase of channel 2 may be different. Channel 3 may also have a frequency of, for example, 14.2 Hz, but there is a phase difference from channel 2. Channel N has a frequency of, for example, 20 Hz and a pulse width and a phase that are adjustable. In actual operations, each of the channels may be separately operated or turned off.

Figure 6A:
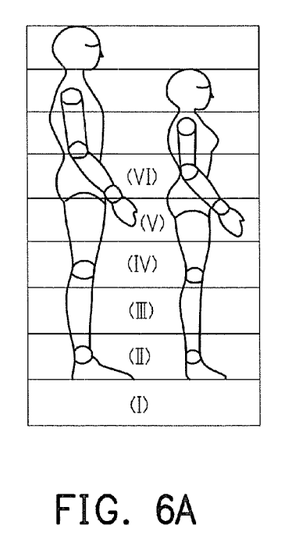
FIG. 6A is a schematic diagram showing regions corresponding to parts of a human body according to an exemplary embodiment of the disclosure.
Figure 6B:
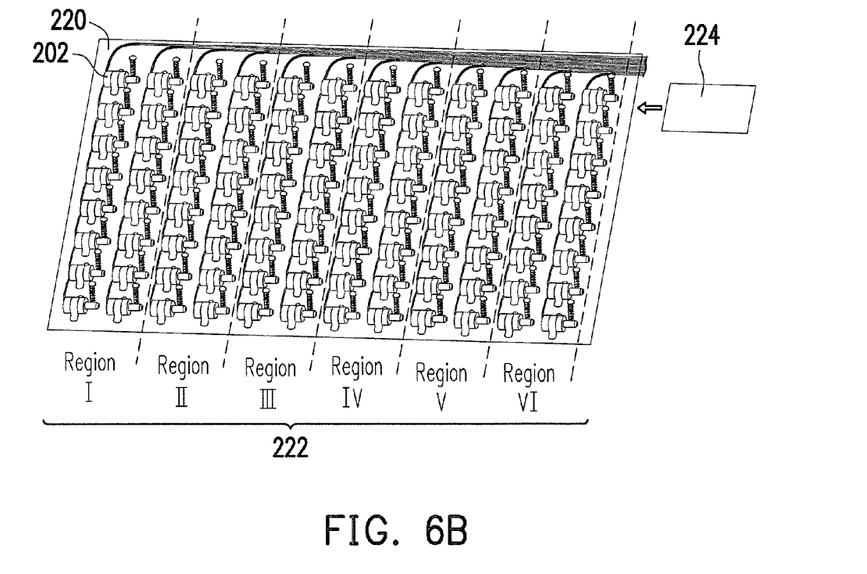
FIG. 6B is a schematic diagram showing a configuration of the resonant regions of the resonant wave generating module corresponding to the body parts depicted in FIG. 6A according to an exemplary embodiment of the disclosure.

FIG. 6A is a schematic diagram showing regions corresponding to parts of a human body according to an exemplary embodiment of the disclosure. FIG. 6B is a schematic diagram showing a configuration of the resonant regions of the resonant wave generating module corresponding to the body parts depicted in FIG. 6A according to an exemplary embodiment of the disclosure. Referring to FIG. 6A, for example, an average height of an ordinary male body illustrated at the left side is considered. In this case, the male body is divided into a plurality of resonant regions, such as six resonant regions, I-VI, according to different positions of the male body. Illustrated at the right side are the resonant regions corresponding to an average height of an ordinary female body. In the present exemplary embodiment, the resonant region I-VI are, for example, as follows:
 a first region, located in a region of foot soles;
 a second region, located in a region of ankles;
 a third region, located in a region of calves;
 a fourth region, located in a region of knees;
 a fifth region, located in a region of thighs; and
 a sixth region, located in a region of the abdomen.

Referring FIG. 6B with FIG. 6A, among the aforementioned multiple resonant devices 120 capable of generating vibrations, motors 202 are taken as the representative. The motor 202 is disposed on a fastening substrate 220. On an array region 222 of the fastening substrate 220, the motor 202 is arranged in strip arrays corresponding to the resonant regions I-VI. Control elements, such as a power supply element and a control plate, are disposed in a control region 224 of the fastening substrate 220. The fastening substrate 220 may be formed by a rigid material or a soft material, wherein the soft material may be adapted to the structure of a main apparatus, such as a massage chair or any other pressure relief apparatus, so as to approach the human body for generating the Schumann waves.

Figure 7:
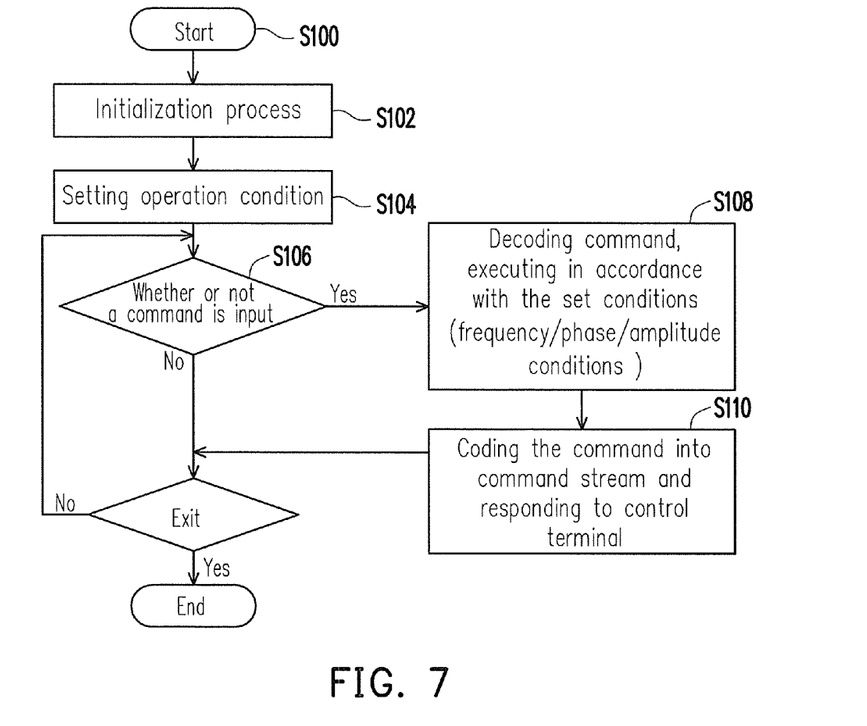
FIG. 7 is a flowchart showing a process of operating the pressure relief apparatus with brain entrainment according to an exemplary embodiment of the disclosure.

An operating process of the pressure relief apparatus is, for example, illustrated in FIG. 7. FIG. 7 is a flowchart showing an operating process of the pressure relief apparatus with brain entrainment according to an exemplary embodiment of the disclosure. The process starts from step S100. In step S102, an initialization process is performed and required default data is downloaded. The initialization process is, for example, to set a format for communicating with a PC end. In step S104, operation conditions, such as usage time, interruption conditions and so on, are set. In step S106, whether or not a command is actually input is judged. If the command is not issued, it is judged that whether the procedure ends due to exit or the procedure is still waiting for the input of the command. Namely, whether the PC end issues a command is continuously checked. In step S108, if the command is issued, the command is decoded and corresponding parameter settings, such as "on or off", frequency, phase, "amplitude of each channel", are executed. In step S110, the command is coded as a command stream and responds to the PC end for conformation. Then, the process returns to the step of examining whether the command ends due to exit or the input of the command is still waited for.

Figure 8:
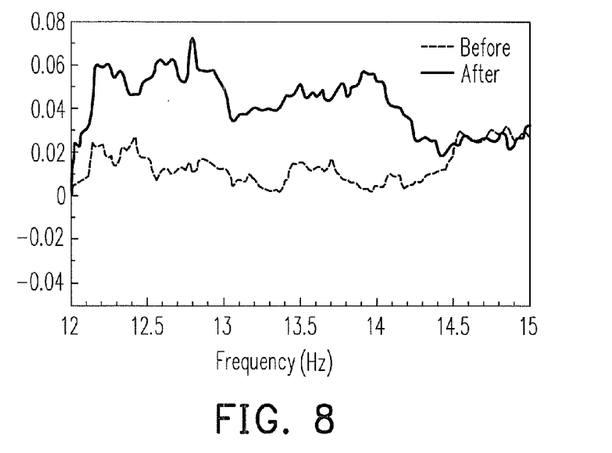
FIG. 8 is a schematic diagram showing changes of energy of sensorimotor rhythm (SMR) according to an exemplary embodiment of the disclosure.

According to actual experiments, the body state is indeed improved by using the pressure relief apparatus with brain entrainment. FIG. 8 is a schematic diagram showing changes of energy of SMR, according to an exemplary embodiment of the disclosure. Referring to FIG. 8, the SMR energy is enhanced after using the pressure relief apparatus with brain entrainment. When the SMR energy is increased, the user's concentration can be enhanced. According to clinical evidence, seizure epilepsy can be mitigated or cognition abilities of aged people can be improved, such that the effect of pressure relief can be achieved.

Hereinafter, how the resonant wave generating module of the pressure relief apparatus with entrainment is associated with physiological signals will be described. A physiological signal is measured by a bio-signal measuring unit, in which at least the energy of autonomic sympathetic nerve system LH and the energy of autonomic parasympathetic nerve system HF of a user are measured. Through analysis by a PC or a micro-processor, a set of feedback control signals is output to the resonant wave generating module according to one of a set of preset conditions so as to modulate resonant devices.

In order to measure the energy of autonomic sympathetic nerve system LH and the energy of autonomic parasympathetic nerve system HF, a commonly known measurement method of lead electrocardiography (ECG) or any other adaptive method may be adopted, and the disclosure is not limited thereto. Referring to the upper part of FIG. 10, here, an example where three resonant regions are activated at once corresponding to body parts is illustrated, and the regions are changed according to difference a between the energy of autonomic sympathetic nerve system LH and the energy of autonomic parasympathetic nerve system HF resulted from changes of physical states of the user.

Table 1 illustrates pressure relief modes activated according to degrees of the difference between the energy of autonomic sympathetic nerve system LH and the energy of autonomic parasympathetic nerve system HF.

TABLE 1

| No. | Conditional formula | Activation frequency | Resonant regions |
|---|---|---|---|
| 1 | LH (%) − HF (%) ≤ 10%, and HF (%) > LH (%) | F1 = 7.83 Hz | I |
| 2 | 10% < LH (%) − HF (%) ≤ 20% | F1 = 7.83 Hz F2 = 14 Hz | I, II |
| 3 | 20% < LH (%) − HF (%) ≤ 30% | F1 = 7.83 Hz F2 = 14 Hz | I, III |
| 4 | 30% < LH (%) − HF (%) ≤ 40% | F1 = 7.83 Hz F2 = 14 Hz F3 = 20 Hz | I, II, III |
| 5 | 40% < LH (%) − HF (%) ≤ 50% | F1 = 7.83 Hz F2 = 14 Hz | II, III |
| 6 | 50% < LH (%) − HF (%) ≤ 60% | F1 = 7.83 Hz | II, III, IV |

TABLE 1-continued

| No. | Conditional formula | Activation frequency | Resonant regions |
|---|---|---|---|
|  |  | F2 = 14 Hz |  |
|  |  | F3 = 20 Hz |  |
| 7 | 60% < LH (%) − HF (%) ≤ 70% | F1 = 7.83 Hz | III, IV, V |
|  |  | F2 = 14 Hz |  |
|  |  | F3 > 20 Hz |  |
| 8 | 70% < LH (%) − HF (%) ≤ 80% | F1 = 7.83 Hz | IV, V, VI |
|  |  | F2 = 14 Hz |  |
|  |  | F3 > 20 Hz |  |
| 9 | 80% < LH (%) − HF (%) ≤ 90% | F1 = 7.83 Hz | IV, V, VI |
|  |  | F2 = 14 Hz |  |
|  |  | F3 > 20 Hz |  |
| 10 | 90% < LH (%) − HF (%) ≤ 100% | F1 = 7.83 Hz | IV, V, VI |
|  |  | F2 = 14 Hz |  |
|  |  | F3 > 20 Hz |  |

Figure 9:
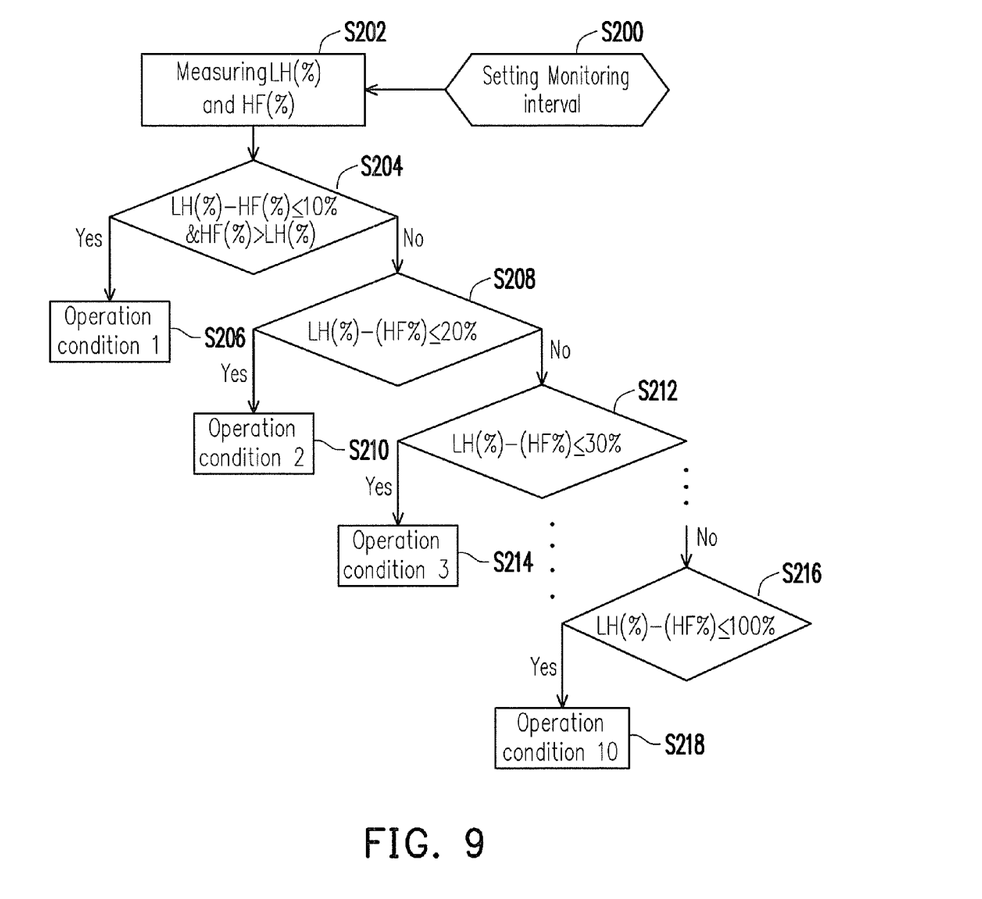
FIG. 9 is a flowchart showing an examining process corresponding to Table 1 according to an exemplary embodiment of the disclosure.

FIG. 9 is a schematic diagram showing an examining process corresponding Table 1 according to an exemplary embodiment of the disclosure. Referring to FIG. 9, in step S200, a monitoring interval is set and then the process enters step S202. In step S202, values of energy of autonomic sympathetic nerve system LH (%) and energy of autonomic parasympathetic nerve system HF (%) are measured. In step S204, it is examined that whether conditions of LH (%)−HF (%)≤10% and HF (%)>LH (%) are satisfied. If the result is "yes", the process enters step S206, and a pressure relief mode conforming to condition NO. 1 is activated. If the result is "no", the process enters step S208, whether condition NO. 2 (i.e., 10%<LH (%)−HF (%)≤20%) is satisfied is examined. If the result is "yes", a pressure relief mode conforming to condition NO. 2 in the step S210 is activated. If the result is "no", the process enters step S212, and whether condition NO. 3 (i.e., 20%<LH (%)−HF (%)≤30%) is satisfied is examined. If the result is "yes", the process enters the step S214, in which a pressure relief mode, conforming to condition NO. 3, is activated. If the result is "no", the process enters step S216, and whether condition NO. 4 (i.e., 30%<LH (%)−HF (%)≤40%) is satisfied is examined, and so on, until the process enters step S218 and the content of condition NO. 10 is performed.

Figure 10:
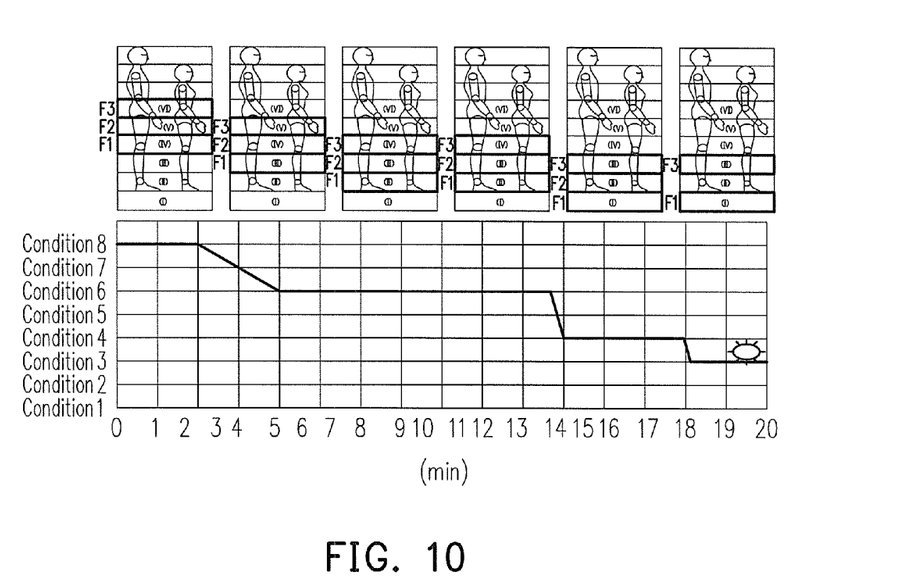
FIG. 10 is a time-evolutional schematic diagram showing a frequency spatial distribution from an initial value to an end value corresponding to a multi-channel Schumann wave of a human body according to an exemplary embodiment of the disclosure.

FIG. 10 is a time-evolutional schematic diagram showing a frequency spatial distribution from an initial value to an end value corresponding to a multi-channel Schumann wave of a human body according to an exemplary embodiment of the disclosure. Referring to FIG. 10, the upper part of the diagram presents positions of a human body activated corresponding to the Schumann wave. The lower part of the diagram presents different conditional segments where changes in physical state of the human body affected by the Schumann wave are generated. To be specific, the human body may not be in a pressure-relieving state in the beginning and need to be led by a Schumann wave that is closer thereto and modulated adjacent to the resonant region VI, such that the human body is relaxed. After a period of time, the physical state is changed and enters another condition and in response thereto, a mode of the Schumann wave is also changed. Finally, the human body reaches a relaxed state.

In the disclosure, for example, output signals containing physiological states are further utilized to control biofeedback with the multi-channel Schumann resonance frequency of so as to achieve a scenario interface architecture for guiding the physiological states.

The pressure relief apparatus with biofeedback for brain entrainment introduced by the disclosure works based on a principle of the biofeedback resulting in brain entrainment. That is, with a guidance process where detected physiological signals are utilized to reflect a current physiological state of an experiencing person, the physical and mental state of the experiencing person is adjusted to a specific target. In addition to quantifying the physiological signals and driving preset entrainment frequencies of the multi-channel Schumann wave according to the feedback message, such biofeedback guidance further includes transferring the quantified results into graphics that are understandable to ordinary people or adapt the results corresponding to scenario designs. By doing so, the experiencing person will have a stronger present sensation and the pressure relief effect will be much increased. Therefore, the scenario interface introduced herein researches on interpreting the autonomic nervous physiological signals, but does not limit the autonomic nervous physiological signals to be the only one input signals. Specially, electromyography (EMG) signals, gravity center of a human body, postures and so forth will be researched and integrated based on demand for intuitive control. That is to say, the guidance of the scenario interface introduced by the disclosure may combine different input information, such that the user may be intuitively guided to control the biofeedback for the entrainment of the multi-channel Schumann wave according to the physiological signals.

Figure 11:
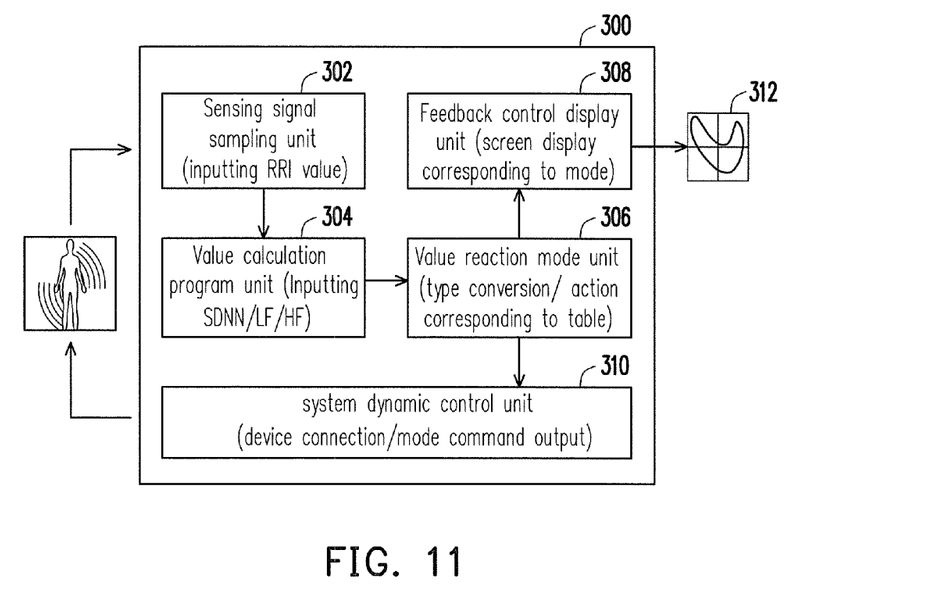
FIG. 11 is a structurally schematic diagram illustrating a scenario interface using autonomic nerve system physiological signals with the control of Google SKY according to one of the scenario designs of an exemplary embodiment of the disclosure.

FIG. 11 is a structurally schematic diagram illustrating a scenario interface using autonomic nerve system physiological signals with the control of Google SKY according to one of the scenario designs introduced by the disclosure. Here, the Google Sky is taken as an example for producing the sky map of stars. The invention is not limited to the use of Google Sky to produce the sky map. Referring to FIG. 11, an idea surfing system 300 operated according to the autonomic nervous physiological signals with idea surfing is introduced and includes a sensing signal sampling unit 302 for the autonomic nerve system physiological signals, a value calculation program unit 304, a value reaction mode unit 306, a feedback control display unit 308 and a system dynamic control unit 310.

The sensing signal sampling unit 302 receives a physiological signal, such as a heartbeat interval (R-R interval, RRI). The value calculation program unit 304 performs real-time value calculations and processing and outputs a variety of signals, such as a heart rate variability coefficient (SDNN), an energy of autonomic sympathetic nerve system LH and an energy of autonomic parasympathetic nerve system HF. The system dynamic control unit 310 changes various state types (such as changes of a display type and an operation of look-up table control) according to values calculated by the value calculation program unit 304. The feedback control display unit 308 outputs a corresponding display mode to control a screen displayed by the display 312. The system dynamic control unit 310 also receives output signals from the value reaction mode unit 306 to adjust a physiological state of a user.

Figure 12:
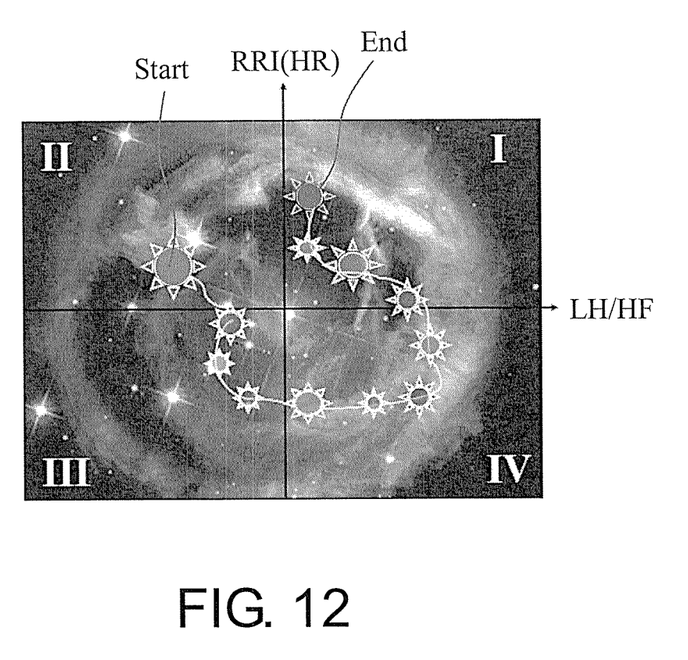
FIG. 12 is schematic diagram illustrating physiological states displayed with Google Sky as the background according to one of the scenario designs of an exemplary embodiment of the disclosure.

The value calculation program unit 304 and the system dynamic control unit 310 calculates a real-time energy related to the autonomic nerve system and a scenario control and display of a sky surfing mode, which is illustrated in FIG. 12.

FIG. 12 is schematic diagram illustrating physiological states displayed with Google Sky as the background according to one of the scenario designs of an exemplary embodiment of the disclosure. Referring to FIG. 12, after the pressure relief apparatus with brain entrainment of the disclosure is connected with a network through the scenario interface, information on the network, such as Google Sky, may be obtained. A currently corresponding state position is updated at any time according to a currently measured physiological state with the scenario of Google Sky. Various types of display modes may be considered, and an example thereof is as follows.

A current autonomic nerve system state of an individual is displayed according to a relationship between a heart rate variability coefficient (SDNN) and a total power (TP) of autonomic nerve system, and that is sizes of astral bodies in Google Sky. Regarding a conscious trajectory regarding physiological signals in sky surfing, path points are determined by the RRI of the user relative to a ratio of the energy of autonomic sympathetic nerve system LH to the energy of autonomic parasympathetic nerve system HF.

In other words, a feature of an autonomic nerve system physiological signal is displayed by using a characteristic astral body having changes of types, such as a color, a size and so on. The astral body is staked on a Google Sky map and moves to different spaces following the conscious trajectory. The user may experience different sky surfing scenarios in the pressure relief space. A change the physiological signal of the experiencing person, which is evolved by time of pressure relief, is represented by a diagram showing the relationship of RRI to LH/HF.

Figure 13A:
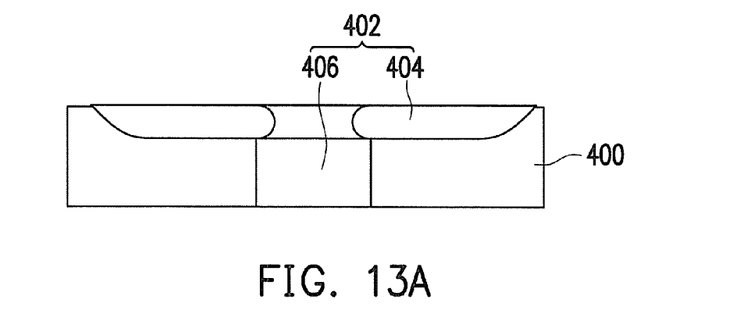
FIGS. 13A-13C are drawings, schematically illustrating physiological states displayed with a flower growth as the background according to one of the scenario designs of an exemplary embodiment of the disclosure.
Figure 13B:
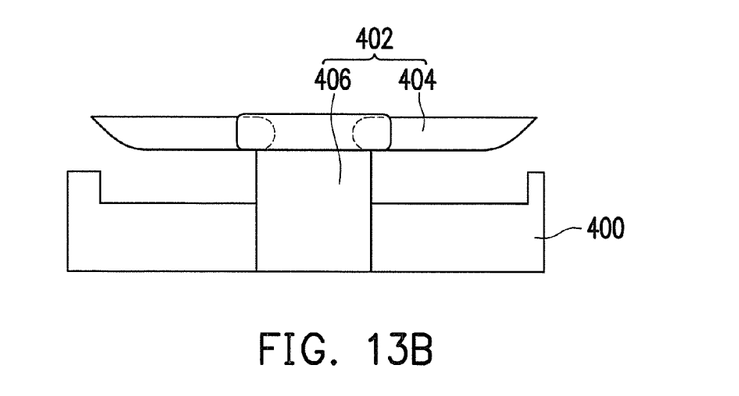
Figure 13C:
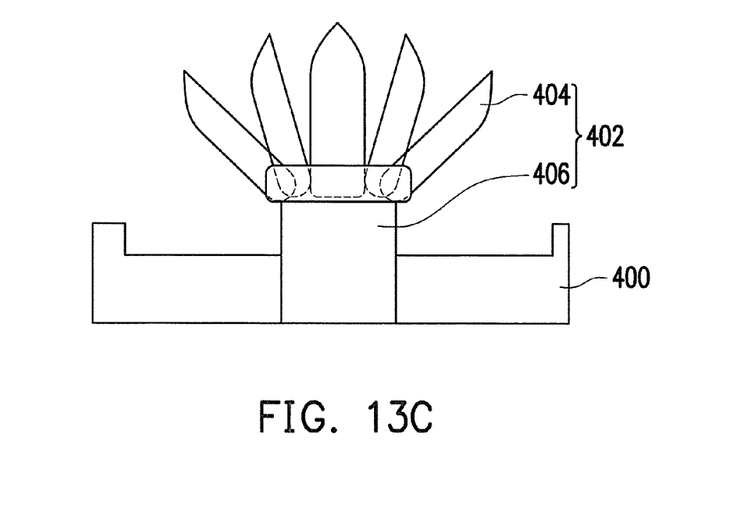

Moreover, in another scenario design similar to that illustrated in FIG. 12, a plant growth state may be adopted. FIGS. 13A-13C are drawings, schematically illustrating physiological states displayed with a flower growth as the background according to one of the scenario designs of an exemplary embodiment of the disclosure.

Referring to FIG. 13A, a physiological state diagram includes, for example, soil 400 and a flower 402. In the beginning, a physiological state is, for example, in a tense state and displayed by the flower 402 with a stem 406 and petals 404 buried into the soil 400. Referring to FIG. 13B, after using the pressure relief apparatus with brain entrainment for a period of time, the physiological state starts to stretch, and the flower 402 starts to grow, the stem 406 comes out from the soil 400, but the petals 404 do not rise yet. Referring to FIG. 13C, further after a period of time, the physiological state of the user is already in relaxed state, and at this time, the petals 404 of the flower 402 present a blossom state to express the scenario. The way of presenting the flower 402 may be adjusted according to actual designs.

In other words, in the pressure relief apparatus with brain entrainment of the disclosure, while feeding back a mode of pressure relief, a mode of displaying a scenario is also obtained from the network or external information through the scenario interface. By the analysis of the physiological state, the displayed scenario state may also be changed at the same time, such that the user may understand the current changes of the physiological state of user. The detailed system architecture and mode analysis of the pressure relief apparatus with brain entrainment may be configured according to actual requirements.

Generally, although the Schumann wave naturally exists in the earth, causing the Schumann wave resonance with the brain wave, however, human body does not always have effective resonance with the Schumann wave because the Schumann wave may be too weak. In the disclosure, the vibrating motors in an array configuration with the specific vibration frequencies, depending on the mental condition of the user be detected, is used to achieve brain entrainment, artificially. As a result, the brains wave, maybe in chaos, can be guided by the vibrating motors with the given vibration frequencies. The artificial frequency immerses into the brain wave to cause the artificially resonance and get approaching to the Schumann wave resonance. The brain entrainment can then be achieved in the disclosure.

It will be apparent to those skilled in the art that various modifications and variations can be made to the structure of the disclosed exemplary embodiments without departing from the scope or spirit of the disclosure. In view of the foregoing, it is intended that the disclosure cover modifications and variations of this disclosure provided they fall within the scope of the following claims and their equivalents.

What is claimed is:

1. A pressure relief apparatus with brain entrainment, consisting of:
   a resonant wave generating module, comprising a plurality of resonant devices divided into a plurality of resonant regions, wherein each of the resonant regions generates a resonant wave having a resonant frequency peak being tunable or turned off respectively, wherein each of a plurality of pulse voltage signals with a given frequency and a corresponding period is applied on a corresponding one of the resonant devices to produce the resonant wave having the resonant frequency peak, wherein each pulse voltage signal turns on the corresponding resonant device once, and the resonant frequency peaks are discrete with the period corresponding to the given frequency of the plurality of pulse voltage signals, and
   a bio-signal sensor unit, at least measuring an energy of autonomic sympathetic nerve system LH and an energy of autonomic parasympathetic nerve system HF, and outputting a set of feedback control signals according to one of a plurality of predetermined conditions to the resonant wave generating module to modulate the resonant devices by at least varying the given frequency of the plurality of pulse voltage signals applied to one or more of the resonant devices.

2. The pressure relief apparatus according to claim 1, wherein each of the resonant waves switches from a first frequency, a second frequency, or a third frequency, wherein the first frequency, the second frequency, and the third frequency respectively corresponding to α band, β1 band and β2 band in a brainwave.

3. The pressure relief apparatus according to claim 2, wherein the resonant regions of the resonant wave generating module are configured according to positions of a plurality of body parts of a human between foot soles and abdomen.

4. The pressure relief apparatus according to claim 3, wherein the plurality of body parts comprises:
   a first region, located in a region of foot soles;
   a second region, located in a region of ankles;
   a third region, located in a region of calves;
   a fourth region, located in a region of knees;
   a fifth region, located in a region of thighs; and
   a sixth region, located in a region of the abdomen.

5. The pressure relief apparatus according to claim 4, wherein a difference value is obtained by the energy of autonomic sympathetic nerve system LH subtracting the energy of autonomic parasympathetic nerve system HF, and one of the predetermined conditions is selected according to a relationship between the difference value and a plurality of threshold values to generate the set of feedback control signals to control each of the resonant waves of the resonant regions.

6. The pressure relief apparatus according to claim 5, further comprise:

when the difference value is less than or equal to 10%, the first region is activated in the first frequency;
when the difference value is greater than 10% and less than or equal to 20%, the first region and the second region are activated in the first frequency and the second frequency, respectively;
when the difference value is greater than 20% and less than or equal to 30%, the first region and the third region are activated in the first frequency and the second frequency, respectively;
when the difference value is greater than 30% and less than or equal to 40%, the first region, the second region and the third region are activated in the first frequency, the second frequency and the third frequency, respectively;
when the difference value is greater than 40% and less than or equal to 50%, the second region and the third region are activated in the first frequency and the second frequency, respectively;
when the difference value is greater than 50% and less than or equal to 60%, the second region, the third region and the fourth region are activated in the first frequency, the second frequency and the third frequency, respectively;
when the difference value is greater than 60% and less than or equal to 70%, the third region, the fourth region and the fifth region are activated in the first frequency, the second frequency and the third frequency, respectively;
when the difference value is greater than 70% and less than or equal to 80%, the fourth region, the fifth region and the sixth region are activated in the first frequency, the second frequency and the third frequency, respectively;
when the difference value is greater than 80% and less than or equal to 90%, the fourth region, the fifth region and the sixth region are activated in the first frequency, the second frequency and the third frequency, respectively; and
when the difference value is greater than 90% and less than or equal to 100%, the fourth region, the fifth region and the sixth region are activated in the first frequency, the second frequency and the third frequency.

7. The pressure relief apparatus according to claim 2, wherein the first frequency is 7.83 Hz, the second frequency is 14 Hz, and the third frequency is 20 Hz or higher.

8. The pressure relief apparatus according to claim 1, wherein the resonant wave generating module activates at least one of the resonant regions, and respectively controls each of the resonant waves of the at least one of the resonant regions according to a change of the set of feedback control signals and one of the predetermined conditions.

9. The pressure relief apparatus according to claim 1, wherein each of the resonant waves switches between a plurality of frequencies corresponding to a plurality of resonant frequencies of a Schumann wave.

10. The pressure relief apparatus according to claim 9, wherein the resonant regions of the resonant wave generating module are configured according to positions of a plurality of body parts of a human between foot soles and abdomen.

11. The pressure relief apparatus according to claim 10, wherein the resonant wave generating module activates at least one of the resonant regions and respectively controls each of the resonant waves of the at least one of the resonant regions according to a change of the set of feedback control signals and one of the predetermined conditions.

12. A pressure relief system, comprising:
the pressure relief apparatus according to claim 1;
an interface unit, receiving the set of feedback control signals to output an image state control signal; and
a display unit, receiving the image state control signal of the interface unit and changing content of a displayed image according to the image state control signal.

13. The pressure relief system according to claim 12, wherein the display unit is operated with a sky map, a position of an indicator is also displayed on the sky map according to a change of the image state control signal.

14. The pressure relief system according to claim 12, wherein the display unit displays a biological activity state diagram according to the change of the image state control signal.

15. The pressure relief apparatus according to claim 1, wherein each of the resonant devices comprises:
a motor, rotating according to the pulse voltage signal having the frequency identical to a frequency of a corresponding one of the resonant waves;
a damping element, coupled to the motor and returning the motor to an original position after rotating; and
a vibrator, disposed on a shaft of the motor and generating a corresponding one of the resonant waves by rotation of the motor.

16. The pressure relief apparatus according to claim 1, wherein the resonant devices are distributed in a plurality of strip units, and a set of multiple adjacent ones of the strip units forms one of the resonant regions.

17. The pressure relief apparatus according to claim 1, wherein the bio-signal sensor unit further measures a heart rate, a coefficient of heart rate variability and a total power of the autonomic nerve system.

18. The pressure relief apparatus according to claim 1, wherein the resonant wave generated in each of the resonant regions having the resonant frequency peak is produced without light.

* * * * *